United States Patent [19]

Katz et al.

[11] Patent Number: 4,476,026

[45] Date of Patent: Oct. 9, 1984

[54] APPARATUS USEFUL IN IDENTIFYING A SOLUTE

[75] Inventors: Elena Katz, Westport; Kenneth L. Ogan, Bethel; Raymond P. W. Scott, Ridgefield, all of Conn.

[73] Assignee: The Perkin-Elmer Corporation, Norwalk, Conn.

[21] Appl. No.: 477,577

[22] Filed: Mar. 21, 1983

[51] Int. Cl.$^3$ ............................................. B01D 15/08
[52] U.S. Cl. ................................... 210/656; 210/198.2
[58] Field of Search ............. 210/635, 656, 101, 198.2

[56] References Cited

U.S. PATENT DOCUMENTS

| | | | |
|---|---|---|---|
| 3,837,217 | 9/1974 | Schulz | 210/635 |
| 3,926,800 | 12/1975 | Stephens | 210/656 |
| 4,353,801 | 10/1982 | Mukoyama et al. | 210/635 |

OTHER PUBLICATIONS

The Chromapack Guide to Chromatography by Chromapack Nederland B.V., pp. 56 and 57, 1981.
High Performance Liquid Chromatography of Vinca Rosea Alkaloids and Correlation of Plate Height and Molecular Weight in Journal of Chromatography, 214 (1981), pp. 95-99.
Estimation of Molecular Weight of Peptides—by Shioya et al. in Journal of Chromatography, 240 (1982), pp. 341-348.

Primary Examiner—John Adee
Attorney, Agent, or Firm—E. T. Grimes

[57] ABSTRACT

An apparatus useful in identifying a solute includes a microbore separation column having unusually large particle packing making up the bed thereof. In addition, the microbore column is excessively long compared to conventional columns. Preferably, the column is thermally stabilized.

1 Claim, 3 Drawing Figures

APPARATUS USEFUL IN IDENTIFYING A SOLUTE

BACKGROUND OF THE INVENTION

The present invention generally relates to an apparatus useful in the identification of a solute and, in particular, relates to such an apparatus including means for determining the molecular weight thereof.

One analytical technique which has been receiving considerable attention in recent history is chromatography; more specifically, liquid chromatography. As it has developed liquid chromatography has become quite sophisticated not only in its ability to separate complex organic mixtures but to accomplish the separation quickly. To date, major emphasis has been placed on both the overall chromatographic systems, i.e., the pump, the solvent mixing, etc., and the separating columns themselves. As one would reach a new capability the other would be improved to keep pace.

These considerable advances notwithstanding, the identification of a solute, as a result of comparing the chromatogram, i.e., direct chromatographic data, of the unknown sample to the chromatogram of known standards, is relatively inaccurate. In fact, the identification of an unknown in this fashion is so unreliable that most identifications occur as a result of first isolating the solute of interest and then performing another, more accurate, analytical technique on that sample. For example, isolated solutes are frequently identified by infrared spectroscopy or by use of mass spectrometry.

Such identification procedures are time consuming and expensive but also complicated. Thus, the need to enhance the identification of a solute directly from chromatographic data is paramount.

SUMMARY OF THE INVENTION

Accordingly, it is one object of the present invention to provide an apparatus which significantly enhances the identification of a solute directly from the chromatographic data.

This object is accomplished, at least in part, by an apparatus including a chromatographic separating device and a means for determining the molecular weight of a solute.

Other objects and advantages will become apparent from the following detailed description read in connection with the attached drawing and the claims appended hereto.

BRIEF DESCRIPTION OF THE DRAWING

The drawing, not drawn to scale, includes.

DETAILED DESCRIPTION OF THE INVENTION

Figure 1:
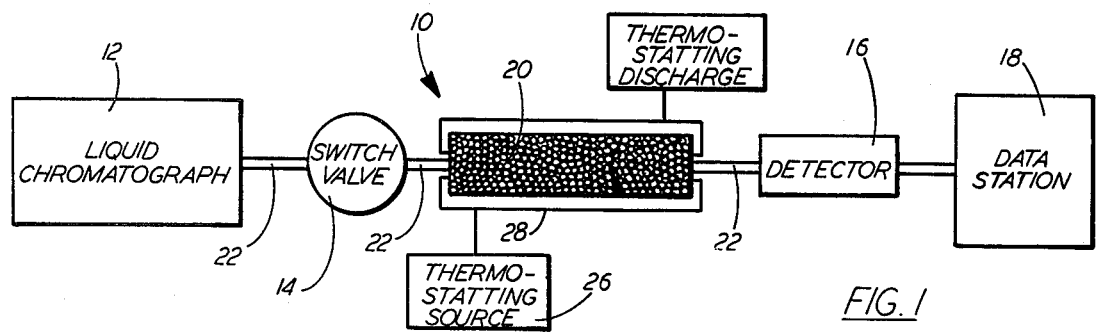
FIG. 1, which is a block diagram of an apparatus embodying the principles of the present invention.

An apparatus, generally indicated at 10 in FIG. 1 and embodying the principles of the present invention, includes a liquid chromatograph 12, an injection valve 14, a liquid chromatography detector 16 and a means 18 for performing operations upon data received from the detector 16. The apparatus 10 further includes a separating column 20, the temperature of which column is thermostatically controlled.

The liquid chromatograph 12 can be any commercially available liquid chromatograph; however, it is preferred that the chromatographic system 12 and its conventional associated system be such as to have a minimum dispersion characteristic. One such pump system is the Series 3B manufactured and marketed by The Perkin-Elmer Corporation, Norwalk, Conn. The injection valve 14, detector 16 and data manipulation means 18 can also be conventional commercially available elements. For reasons more fully discussed below, it is preferred that each element between the pump (not shown) of the chromatograph 12 and the data station 18 also be such as to minimize extra-column band dispersion. For example, low dispersion connecting tubes 22 are preferably employed.

The column 20 preferably has an inside diameter less than about 2 mm and which has a length on the order of about 1 meter. The column 20 is preferably packed with relatively large particles, such as, for example, particles having an average diameter on the order of about 20 microns. In one particular embodiment, the packing bed 22 is a silica gel.

The column 20 is maintained during operation at a particular temperature by means of a thermostatting system 26 which, in the preferred embodiment, includes a water jacket 28 having circulating water passing therethrough which water jacket 28 surrounds the separating column 20. In such an arrangement, the thermostatting means 26 can be provided with a circulating pump mechanism, as well as a reservoir system. Alternatively, as well known in the art, the reservoir system, after absorbing heat from the column 20, may be directly returned into the circulating pump mechanism for further circulation through the thermal jacket 28.

For reasons more fully discussed below, the liquid chromatograph 12 is operated so as to provide a linear velocity flow rate of about 1 cm/second of the sample/solvent mixture through the column 20.

The data manipulation means 18 includes therein means for determining the dispersion of a chromatographic peak and additionally means for determining the approximate, i.e. generally within 10%, molecular weight of a particular solute based upon a first order relationship between the previously determined dispersion and the molecular weight. Such a determining means enhances the identification of the solute. Although the means 18 for manipulating data has been described herein as containing the dispersion determining means and the molecular weight determining means, other elements could also be substituted therefor. For example, a chart recorder can be employed and by appropriate measurement provide the dispersion information.

It will undoubtedly have been recognized at this juncture that the combination of the column inside diameter, its packing, its length and the linear velocity of the mobile phase passing therethrough are quite contrary to what is normally expected in the field of liquid chromatography. Nevertheless, it is these differences which constitute the apparatus 10. Consequently, a review of peak analysis and column characteristics is provided hereinafter.

In chromatography, a chromatographic peak can be characterized by its variance, which variance is proportional to the square of its width. Mathematically, this is akin to the square of the standard deviation of a Gaussian bell-shaped curve. In chromatography, it is generally understood that the width of the peak is primarily a function of the dispersion of the band throughout the system.

In column technology, the band dispersion is affected by three distinct processes within the separation column. The first process, i.e., the multipath dispersion, is caused by the molecules of the solute meandering between the particles of the packed bed. In so doing, the paths each molecule takes is different from that of each other molecule, i.e., some molecules travel shorter distances through the column while others travel longer distances. The multipath dispersion is dependent upon the nature of the particle diameters of the packing and is independent of the solvent of the mixture. The second dispersion process, i.e., longitudinal diffusion, results from the molecules of a particular solute spreading out within the mobile phase during the time that they are in the column. The spreading depends upon the residence time of the solute in the column and thus is inversely proportional to the linear velocity of the mobile phase. Consequently, this effect can be minimized by employing a high linear velocity for the mobile phase. The third dispersion process is generally known as the resistance-to-mass transfer dispersion, and this is caused by the fact that during passage through the column, a particular solute is distributed between a stationary phase and a mobile phase. At any given time, some molecules are resident in the stationary phase. Consequently, as the mobile phase continues through the column, the molecules remaining in the mobile phase move downstream from those in the stationary phase. It has been determined that this spreading process is inversely proportional to the solute diffusivity and directly proportional to both the square of the particle diameter and the linear velocity. Consequently, at high linear velocities employing particles of relatively large diameter, the resistance-to-mass transfer dispersion process can be made the dominant. Further, it is known that the inverse of diffusivity is related to the molecular weight of the solute.

Thus, if one wishes to ascertain the diffusivity and consequently the molecular weight, one preferable operating condition should be a high linear velocity for the mobile phase, since that condition enhances the resistance-to-mass transfer but reduces the longitudinal diffusion. Since the multipath effect is independent of the linear velocity of the mobile phase, the variance of the band of solute eluted from the column operated at high linear mobile phase velocities, has been found to be predominantly related to the molecular weight of that solute. As mentioned above, the knowledge of the molecular weight of a particular solute considerably enhances its accurate identification directly from the chromatographic data rather than depend upon other, more expensive, identification techniques.

Figure 2:
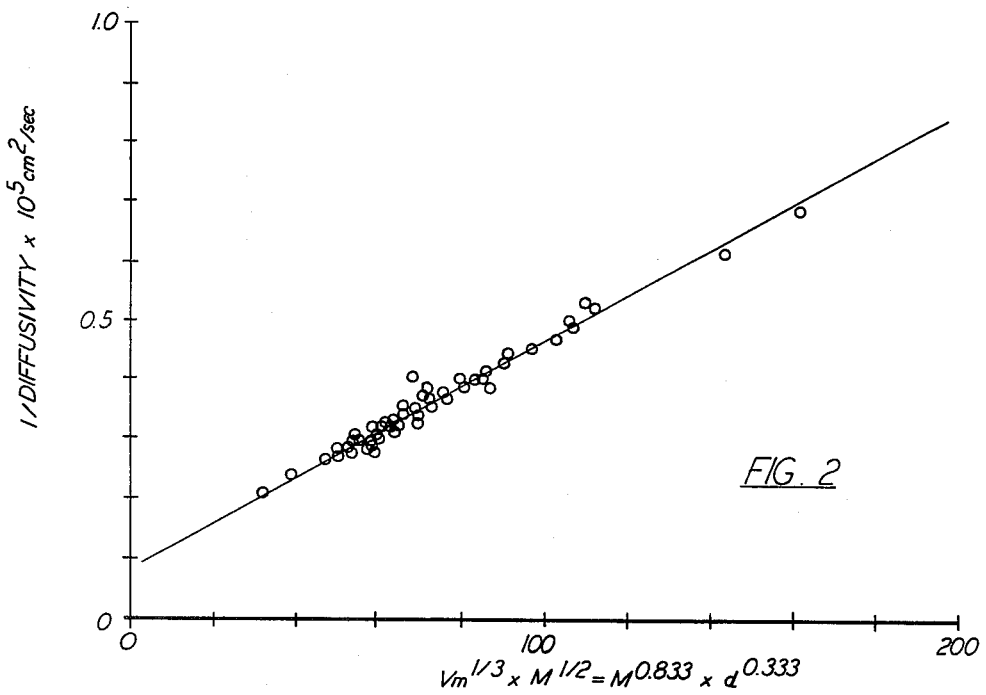
FIG. 2, which is a graph of the reciprocal of diffusivity versus a function of the molecular weight.

In order to ascertain the accuracy of the above theory, the relationship between diffusivity of a particular solute in the mobile phase and its molecular weight was determined. This was necessary for correlation between the peak dispersion of a particular solute with the molecular weight thereof. In order to ascertain this data, the column shown in FIG. 1 was replaced with a straight tube and consequently, chromatographic separation effects were substantially completely removed. The dispersion of the chromatographic system was measured using a straight tube having an inside diameter on the order of about 0.2 mm, which tube was about 5.6 cm long. The mobile phase or solvent used was a 5% volume/volume solution of ethyl acetate in n-hexane. The dispersion of this system was determined to be on the order of about 1.3 $\mu L^2$. Subsequently, the diffusivities of about 70 solutes were measured utilizing a straight tube having an inside diameter of about 0.4 mm, which was approximately 3.7 meters long. During these experiments, the straight tube was maintained at a temperature of about 25° C. and a mobile phase flow rate of about 0.5 mL/minute was maintained. The results of this investigation are most clearly demonstrated in FIG. 2. FIG. 2 is a graph of one over the diffusivity versus the product of the cube root of the molar volume and the square root of the molecular weight of each solute. As can be seen, this is a first order relationship and, as noted, all measurements were within an absolute error of approximately 10%.

Figure 3:
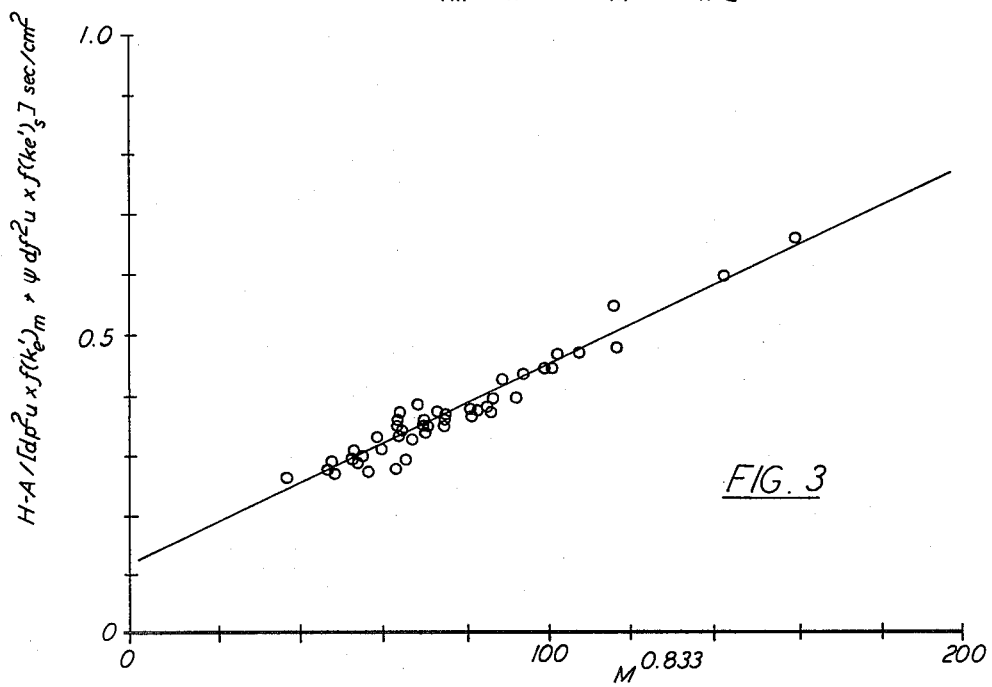
FIG. 3, which is a graph of peak dispersion, corrected for the retention function, versus a function of molecular weight.

Once this first order relationship was ascertained, the same 70 solutes were measured under chromatographic conditions. Specifically, a column, generally referred to as a microbore column, having an inside diameter on the order of about 1 mm and which was approximately 1 meter long, was packed with silica gel particles having an average diameter of about 20 microns. Since the linear velocity of the mobile phase was about 1 cm/second in order to enhance the resistance-to-mass phenomenon and make it dominant, the temperature within the column increased. In order to maintain the column at a relatively constant temperature, the column was thermostatted in a water jacket being fed with water at approximately 25° C. temperature. The solvent used in these experiments was 5% ethyl acetate in n-hexane. As a consequence of the chromatographic separation, the solutes of interest eluted from the column at a different time. Thus, the peak dispersion of each solute was corrected for the retention time. Consequently, a corrected peak dispersion was plotted against the molecular weight. Again, the linear relationship found permitted the molecular weight to be determined within 10% of the absolute error in 90 percent of the substances studied. This relationship is shown in FIG. 3. The 70 compounds tested were selected from a number of well known groups of compounds. Specifically, the compounds examined represent the following groups of compounds:

aromatic hydrocarbons;
aldehydes, ketones, esters, ethers;
nitro- and dinitrocompounds;
chloro-, bromo- and fluorocompounds;
polycyclic aromatic hydrocarbons;
condensed polycyclic aromatic hydrocarbons;
polycyclic aromatic hydrocarbons with functional groups such as nitro-, methoxy-, cyano-, ketogroups;
heterocyclic compounds containing sulfur, nitrogen, oxygen in the ring;
compounds containing phosphorus and sulfur in the functional groups;
compounds containing double bonds in the functional groups; and
one aromatic secondary amine and one azocompound.

As a consequence of these experiments, a relationship was determined which is normalized for the retention behavior of a given solute in a given chromatographic system and which represents the straight line curve between the peak dispersion as plotted against the molecular weight of the solute. This relationship is referred to as the normalized, (i.e. corrected for retention behavior) peak dispersion of a given solute in the above-described chromatographic system and can be mathematically represented as:

$$H = A/[dp^2 u \times f_m(k_e') + \psi df^2 u \times f_s(k_e')] \times 10^5 \text{ sec/cm}^2$$

wherein:
H is the peak variance per unit length measured for each solute (in our experiment the H range was from 0.025 cm to 0.07 cm).
dp is the particle diameter (ours - mean particle diameter was 17.5 micrometer).
A is the multipath term defines the quality of the packing procedure (in our experiment it was about 5 dp).

$$k_e' = \frac{t_r - t_e}{t_e}$$

where $t_r$ retention time of given solute eluted from the column (range of $k_e'$ was from 0.6 to 30.0) and $t_e$-retention time of the fully excluded nonpermeating solute.

$f_m(k_e')$ is the retention function in the mobile phase; using the well-known Golay retention function:

$$f_m(k_e') = \frac{1 + 6k_e' + 11k_e'^2}{24(1 + k_e')^2}$$

$f_s(k_e')$ is the retention function in the stationary phase; using van Deemter retention function:

$$f_s(k_e') = \frac{8}{\pi^2} \frac{k_e'}{(1 + k_e')^2}.$$

$\psi$ is a constant equal to $1/\alpha$, where $\alpha$ is about equal to 1 as the contents of the pores of the particles are chemically and physically very similar to that of the mobile phase.
u is the mobile phase linear velocity at which we operated. (u=0.98 cm/sec in our experiment).
dp and df (which are the particle diameter and the film thickness, of the stationary phase, respectively) were found by a curve fitting procedure to the van Deemter equation as:

dp=14.4 micrometer and df=10.3 micrometer which is in reasonable agreement with the defined particle size of about 17.5 micrometers.

Once this equation is known, then for a given chromatographic system, i.e., a particular column operated at a particular velocity and having a particular particle diameter, the only unknown factors are the H itself and the multipath term. Consequently, from the knowledge of this equation and chromatographic data obtained in conventional chromatography, the molecular weight of a particular solute can be directly determined from a first order linear relationship. In the practical sense, such an equation can be implemented by means of software systems or alternatively by direct calculation and subsequent comparison plotting against a known calibration curve. Nevertheless, the fact that the system necessarily operates in a previously undesired mode in order to enhance the resistance-to-mass transfer dispersion mechanism such that it is dominant is quite novel. It will be recognized by those skilled in the art that should any of the system factors be changed, other calibration curves may be easily constructed from use of the above equation and since it is a first-order relationship few points need be determined to obtain the resultant increased accuracy in solute identification directly from chromatographic data.

Although the present invention has been described with respect to a single apparatus under specific operating conditions, it will be understood that other conditions and arrangements can be easily utilized without departing from the scope and spirit of the present invention. Consequently, this description is deemed exemplary and not limiting, and the present invention is deemed limited only by the appended claims and the reasonable interpretation thereof.

What is claimed is:
1. A method for enhancing the identification of a solute; said method comprising the steps of:
chromatographically separating a mixture including said solute under conditions where the resistance-to-mass transfer dispersion process is the dominant factor in the total column band dispersion;
determining the dispersion of the resultant chromatographic peak; and
determining the molecular weight of said solute from a first order relationship between said dispersion and said molecular weight whereby solute identification is enhanced.

* * * * *